(12) United States Patent
Kim et al.

(10) Patent No.: US 11,564,663 B2
(45) Date of Patent: Jan. 31, 2023

(54) ULTRASOUND IMAGING APPARATUS AND CONTROL METHOD THEREOF

(71) Applicant: SAMSUNG MEDISON CO., LTD., Hongcheon-gun (KR)

(72) Inventors: Hyungjoo Kim, Seongnam-si (KR); Yeongkyeong Seong, Seoul (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 991 days.

(21) Appl. No.: 16/018,632

(22) Filed: Jun. 26, 2018

(65) Prior Publication Data

US 2018/0368812 A1   Dec. 27, 2018

(30) Foreign Application Priority Data

Jun. 26, 2017   (KR) .................. 10-2017-0080581
Nov. 24, 2017  (KR) .................. 10-2017-0157976

(51) Int. Cl.
  *A61B 8/00*  (2006.01)
  *G16H 50/20*  (2018.01)
  (Continued)

(52) U.S. Cl.
  CPC ............. *A61B 8/54* (2013.01); *A61B 8/085* (2013.01); *A61B 8/465* (2013.01); *A61B 8/467* (2013.01);
  (Continued)

(58) Field of Classification Search
  CPC .......... G06T 7/00; G06T 7/60; A61B 8/0883; A61B 8/467; A61B 8/464; A61B 6/12; A61B 8/445; A61B 8/54; A61B 8/0841; A61B 8/465; A61B 8/06; A61B 8/52; A61B 8/463; A61B 8/12; A61B 8/0891; A61B 5/0066; A61B 8/4438; A61B 5/027;
  (Continued)

(56) References Cited

U.S. PATENT DOCUMENTS

| | | | |
|---|---|---|---|
| 5,553,620 A * | 9/1996 | Snider ................ | G01S 7/52036 600/440 |
| 5,555,534 A * | 9/1996 | Maslak ............... | G01S 15/8979 367/7 |

(Continued)

FOREIGN PATENT DOCUMENTS

| | | |
|---|---|---|
| JP | 2007524461 A | 8/2007 |
| JP | 2014-213030 A | 11/2014 |

OTHER PUBLICATIONS

Communication dated Oct. 17, 2018, issued by the European Patent Office in counterpart European Application No. 18179656.6.
(Continued)

*Primary Examiner* — Oommen Jacob
(74) *Attorney, Agent, or Firm* — Sughrue Mion, PLLC

(57) ABSTRACT

An ultrasound imaging apparatus and a control method thereof. The ultrasound imaging apparatus may include: a display; a communication unit; and a processor configured to be operatively connected to the display and the communication unit. The processor may obtain a first ultrasound image of a subject and a result of an analysis of the first ultrasound image. The processor may also control the display to display a user interface, which allows selection of an operating mode of the ultrasound imaging apparatus, based on the result of the analysis.

15 Claims, 12 Drawing Sheets

(51) Int. Cl.
  *A61B 8/08*    (2006.01)
  *G01S 7/00*    (2006.01)
  *G01S 7/52*    (2006.01)
  *G16H 30/40*   (2018.01)
  *G16H 40/63*   (2018.01)
  *G06N 3/08*    (2006.01)
  *G06N 5/04*    (2006.01)

(52) U.S. Cl.
  CPC .............. *A61B 8/485* (2013.01); *A61B 8/488* (2013.01); *A61B 8/5215* (2013.01); *A61B 8/5223* (2013.01); *A61B 8/565* (2013.01); *A61B 8/585* (2013.01); *G01S 7/003* (2013.01); *G01S 7/52084* (2013.01); *G01S 7/52098* (2013.01); *G06N 3/08* (2013.01); *G06N 5/046* (2013.01); *G16H 30/40* (2018.01); *G16H 40/63* (2018.01); *G16H 50/20* (2018.01)

(58) Field of Classification Search
  CPC ..... A61B 5/0084; A61B 5/0215; A61B 5/318; A61B 5/743; A61B 8/08; A61B 8/4444; A61B 8/5292; A61B 8/468; A61B 8/461; A61B 8/10; A61B 8/469; A61B 8/488; A61B 8/565; A61B 8/02; A61B 8/486; A61B 8/00; G01S 7/52098; G01S 7/52036; G01S 7/52073; G01S 7/5206; G01S 7/53; G06Q 10/10; G16H 40/20; G16H 80/00; G16H 40/67; G16H 15/00; G16H 10/60
  See application file for complete search history.

(56) References Cited

U.S. PATENT DOCUMENTS

| | | | | |
|---|---|---|---|---|
| 5,724,974 A * | 3/1998 | Goodsell, Jr. | ............ | A61B 8/06 600/455 |
| 6,176,830 B1 * | 1/2001 | Freiburger | .......... | G01S 7/52071 600/453 |
| 6,458,081 B1 * | 10/2002 | Matsui | ................... | A61B 8/463 600/437 |
| 7,578,792 B2 * | 8/2009 | Lee | .......................... | A61B 8/06 600/455 |
| 7,912,528 B2 | 3/2011 | Krishnan et al. | | |
| 9,349,098 B1 | 5/2016 | Tonson | | |
| 9,918,701 B2 * | 3/2018 | Hedlund | ............... | A61B 5/0035 |
| 2004/0147840 A1 * | 7/2004 | Duggirala | ............ | G06T 7/0012 600/437 |
| 2004/0204649 A1 * | 10/2004 | Ramraj | ................... | A61B 8/565 600/437 |
| 2004/0254439 A1 * | 12/2004 | Fowkes | ................. | G01S 7/5205 600/407 |
| 2005/0021375 A1 * | 1/2005 | Shimizu | ................. | G06Q 10/10 705/2 |
| 2006/0079778 A1 | 4/2006 | Mo et al. | | |
| 2009/0074280 A1 * | 3/2009 | Lu | ............................ | A61B 8/08 382/131 |
| 2009/0093717 A1 * | 4/2009 | Carneiro | ................... | G06T 7/11 600/443 |
| 2012/0065508 A1 * | 3/2012 | Gerard | ................... | A61B 8/461 600/443 |
| 2013/0184584 A1 * | 7/2013 | Berkey | ................ | A61B 8/5292 600/441 |
| 2014/0177935 A1 * | 6/2014 | Nair | ....................... | A61B 8/445 382/132 |
| 2015/0005630 A1 * | 1/2015 | Jung | ...................... | A61B 8/469 600/437 |
| 2016/0113630 A1 * | 4/2016 | Chang | ................... | G06T 3/0012 600/440 |
| 2017/0262982 A1 * | 9/2017 | Pagoulatos | ........... | A61B 8/469 |
| 2018/0330518 A1 * | 11/2018 | Choi | ..................... | G16H 30/20 |
| 2018/0368812 A1 * | 12/2018 | Kim | ...................... | A61B 8/467 |

OTHER PUBLICATIONS

Communication dated Oct. 25, 2022 issued by the Korean Intellectual Property Office in Korean Application No. 10-2017-0157976.

* cited by examiner

FIG. 5

CPT Code Guidelines Ultrasound ~ 501

Ultrasound Abdomen
76700 Abdomen Complete Ultrasound
76705 Abdomen Limited
93975 Abdomen Doppler
76770 Aorta/Renal Retroperitoneal Complete
76775 Aorta/Renal Retroperitoneal Limited

Ultrasound Extremity
93925 Arteries Legs Bilateral
93923 Arteries Upper or Lower Ext (ABI) Multiple
93926 Arteries Leg Unilateral
93923 Arteries Upper or Lower Ext (ABI) Multiple
93922 Arteries Upper or Lower Ext (ABI) Single
93970 Vein Bilateral or Venous Insufficency-Leg or Arms
93965 Non-Invasive Study Leg Veins with 93970
76881 Soft Tissue Extremity or Axillary Complete
76882 Soft Tissue Extremity or Axillary Limited
93923 Arteries Upper or Lower Ext (ABI) Multiple
93922 Arteries Upper or Lower Ext (ABI) Single
93970 Vein Bilateral or Venous Insufficency-Leg or Arms
93930 Artery Arm Bilateral
93931 Artery Arm Unilateral
76881 Soft Tissue Extremity or Axillary Complete
76882 Soft Tissue Extremity or Axillary Limited

Ultrasound General
76870 Genitalia/Scrotal
76830 Transvaginal
76856 Privic
76857 Bladder
27094 Hip Injection

Ultrasound Breast
76645 Breast U/S
19100 U/S Guided Breast Bx
19000 Breast Aspiration

Ultrasound Chest
76604 Chest

Ultrasound OB
76801 Pregnancy (OB) < 12 weeks
76805 Pregnancy (OB) > 12 weeks
76810 Pregnancy (OB) Twins
76817 Pregnancy (OB) Transvaginal

Echocardiography
93307 Echocardiography

Ultrasound Thyroid
76536 Thyroid
60001 Thyroid FNA

Ultrasound Carotid
93880 Carotid

FIG. 6A

```
┌─────────────────────────┐
│        Protocol         │
├─────────────────────────┤
│                         │
│ • Right mesenchymal boundary    ~601
│   - Lower portion       │
│   - Upper side          │
│   - Right side          │
│ • Hepatic vein          │
│   - HV branch           │
│                         │
│ • Portal Vein           │
│   - PV branch           │
│                         │
│ • Left mesenchymal boundary
│   -Lower side           │
│   -Upper side           │
│   -Left side            │
│                         │
│ • Gallbladder           │
│   -Biliary tract        │
│                         │
│ • Duodenal shadow       │
│ • Right kidney          │
│   -Kidney medulla       │
│   -Kidney cortex        │
│   -Upper portion of kidney
│   -Middle portion of kidney
│   -Lower portion of kidney
│                         │
└─────────────────────────┘
```

Shearwave

Doppler

FIG. 10C

The additional examination was requested for the patient named XXX.
Will you approve the execution of the additional examination?

Yes  No

Please select the required additional examination.

Shearwave  Doppler

1009

ULTRASOUND IMAGING APPARATUS AND CONTROL METHOD THEREOF

CROSS-REFERENCE TO RELATED APPLICATION

This application is based on and claims priority under 35 U.S.C. § 119(a) to Korean Patent Application Serial Nos. 10-2017-0080581 & 10-2017-0157976, which were filed in the Korean Intellectual Property Office on Jun. 26, 2017 & Nov. 24, 2017, respectively, the disclosures of which are hereby incorporated by reference in their entirety.

TECHNICAL FIELD

The disclosure relates to an ultrasound imaging apparatus and a control method thereof.

BACKGROUND

An ultrasound imaging apparatus irradiates an ultrasound signal, which is generated by a transducer of a probe, to a subject (e.g., a patient), receives information of an echo signal reflected from the subject, and obtains an image of an area (e.g., soft tissue or blood flow) inside the subject. Particularly, the ultrasound imaging apparatus is used for medical purposes, such as observation of internal areas of a subject, detection of foreign substances (e.g., a lesion), evaluation of injuries, and the like. As compared to a diagnostic apparatus using X-rays, the ultrasound imaging apparatus is advantageous because it has high stability, can display an image in real time, and is safe because it involves no exposure to ionizing radiation. Accordingly, ultrasound imaging apparatuses can be used together with another imaging diagnostic apparatus, such as a Computerized Tomography (CT) apparatus, a Magnetic Resonance Imaging (MRI) apparatus, and the like.

A clinician who has treated a patient can request an examination using the ultrasound imaging apparatus, and a radiologist or sonographer can perform ultrasonography using an ultrasound imaging apparatus.

When a radiologist performs ultrasonography, the radiologist usually reads the produced images simultaneously with the ultrasonography. However, when a sonographer performs ultrasonography, the sonographer merely manipulates an ultrasound imaging apparatus and does not read the produced images with the level of skill of a doctor. Therefore, the sonographer obtains images required for reading and stores the acquired images in a memory, and then transmits the stored images to a radiologist. The doctor or radiologist then reads the images and makes a diagnosis on the basis of the received images.

Meanwhile, interest in Artificial Intelligence (AI) has recently been increasing. In AI technology, machines learn and draw conclusions by themselves, and recognition rates thereof improve over time through learning or training. AI technology has different types of learning: an unsupervised learning model using an algorithm for autonomously classifying/learning the characteristics of input data; a supervised learning network model using learned data; and the like, and includes element techniques describing (or, corresponding to) functions, such as recognition, decision, and the like of the human brain.

Element techniques may include at least one of, for example, a linguistic understanding technique for recognizing human languages/letters, a visual understanding technique for recognizing things as in the manner of a human visual sense, an inference/prediction technique for determining information to make a logical inference and make a prediction, a knowledge expression technique for processing human experience information as knowledge data, and an operation control technique for controlling autonomous driving of an automobile or the movement of a robot. Among them, the visual understanding technique is for recognizing things as in the manner of a human visual sense and processing the visual recognition, and may include object recognition, object tracking, image search, recognition of a human, understanding of a scene, spatial understanding, image improvement, and the like.

SUMMARY

When a sonographer performs ultrasonography, a case where the sonographer fails to acquire an important image required for a diagnosis may occur. In other words, the sonographer may fail to acquire some images necessary for diagnosis. As a result, a problem may arise in that a doctor (e.g., the radiologist, the clinician), a final reader, becomes incapable of diagnosing a patient's disease, due to an insufficient amount of pertinent information or images.

Also, since a sonographer is an ultrasonography professional, but not a doctor, the sonographer performs ultrasonography only according to a determined protocol without understanding the patient's overall health condition. Accordingly, a problem may arise in that the sonographer cannot immediately respond to the patient's health condition during the ultrasonography and treat the patient.

Also, when ultrasound images that the sonographer has transmitted to a doctor do not include enough information to make a diagnosis, inconvenience may occur in that ultrasonography needs to be re-performed and, to this end, the patient needs to revisit the hospital and repeat the ultrasonography process.

An embodiment of the disclosure provides an ultrasound imaging apparatus and a control method thereof which can provide a user (e.g., a sonographer) with information on acquisition of an additionally-required ultrasound image, and can select an operating mode of the ultrasound imaging apparatus in response to the provided information.

The ultrasound imaging apparatus according to an embodiment of the disclosure can determine, by using AI technology, whether an ultrasound image taken by a sonographer coincides with an image defined by a protocol, and can provide information on an additionally-required ultrasound image or images according to a result of the determination.

According to an embodiment of the disclosure, a determination can be made, by using AI technology, as to whether an ultrasound image taken by a sonographer is an image appropriate for a radiologist or clinician to read for diagnosis of a disease.

According to an embodiment of the disclosure, a determination can be made, by using AI technology, as to whether ultrasonography has been appropriately performed according to a protocol between a clinician and a sonographer, and information on additional ultrasound imaging can be provided when an ultrasound image has been acquired which is inappropriate for reading or does not correctly follow an examination protocol.

In accordance with an aspect of the disclosure, a control method of an ultrasound imaging apparatus is provided. The control method may include: obtaining a first ultrasound image of a subject; obtaining a result of an analysis of the first ultrasound image; displaying a user interface, which allows selection of an operating mode of the ultrasound imaging apparatus, on a display based on the result of the analysis; receiving a user input for selecting the operating mode of the ultrasound imaging apparatus via the user interface; operating the ultrasound imaging apparatus in the operating mode based on the user input; and obtaining a second ultrasound image while the ultrasound imaging apparatus is operating in the selected operating mode.

In accordance with another aspect of the disclosure, an ultrasound imaging apparatus is provided. The ultrasound imaging apparatus may include: a display; a communication unit; and a processor configured to be operatively coupled to the display and the communication unit. The processor may be further configured to: obtain a first ultrasound image of a subject; obtain a result of an analysis of the first ultrasound image; control the display to display a user interface, which allows selection of an operating mode of the ultrasound imaging apparatus, based on the result of the analysis; receive a user input for selecting the operating mode of the ultrasound imaging apparatus via the user interface; operate the ultrasound imaging apparatus in the operating mode based on the user input; and obtain a second ultrasound image while the ultrasound imaging apparatus is operating in the selected operating mode.

In accordance with still another aspect of the disclosure, a computer program product is provided. The computer program product may include a non-transitory computer-readable recording medium storing a program for executing operations including: obtaining a first ultrasound image of a subject; obtaining a result of an analysis of the first ultrasound image by using a learning network model; and displaying a user interface, which allows selection of an operating mode of an ultrasound imaging apparatus, on a display based on the result of the analysis.

In accordance with another aspect of the disclosure, another ultrasound imaging apparatus is provided. The ultrasound imaging apparatus is for imaging a subject and may comprise a processor configured to receive ultrasound images from an ultrasound probe; a display configured to display information; and a communication unit. The processor may be further configured to: transmit, via the communication unit, the received ultrasound images to an external server, receive, via the communication unit, an analysis of the ultrasound images from the external server, wherein the analysis indicates that at least one additional ultrasound image is required, control the display to display an operating mode for operating the ultrasound imaging apparatus or ultrasound probe, receive a user input selecting the operating mode, and control the ultrasound imaging apparatus to obtain the at least one additional ultrasound image while the ultrasound imaging apparatus or ultrasound probe is operating in the selected operating mode.

In accordance with another aspect of the disclosure, yet another ultrasound imaging apparatus is provided. The ultrasound imaging apparatus is for imaging a subject and may comprise a processor configured to receive ultrasound images from an ultrasound probe; a display configured to display information; and a memory storing a learning network model. The processor is further configured to: analyze the received ultrasound images with the learning network model and determine that at least one additional ultrasound image is required, control the display to display an operating mode for operating the ultrasound imaging apparatus or the ultrasound probe, receive a user input selecting the operating mode, and control the ultrasound imaging apparatus to obtain the at least one additional ultrasound image while the ultrasound imaging apparatus or ultrasound probe is operating in the selected operating mode.

BRIEF DESCRIPTION OF THE DRAWINGS

The above and other aspects, features, and advantages of the disclosure will be more apparent from the following detailed description taken in conjunction with the accompanying drawings, in which:

FIG. 5 is a view illustrating an example of an ultrasound image prescription code issued by a doctor;

FIG. 6A is a view illustrating an example of a protocol related to an embodiment of the disclosure;

FIGS. 10C and 10D are views each illustrating an example of an interface displayed on a display of an external electronic apparatus according to an embodiment of the disclosure;

DETAILED DESCRIPTION

Figure 1:
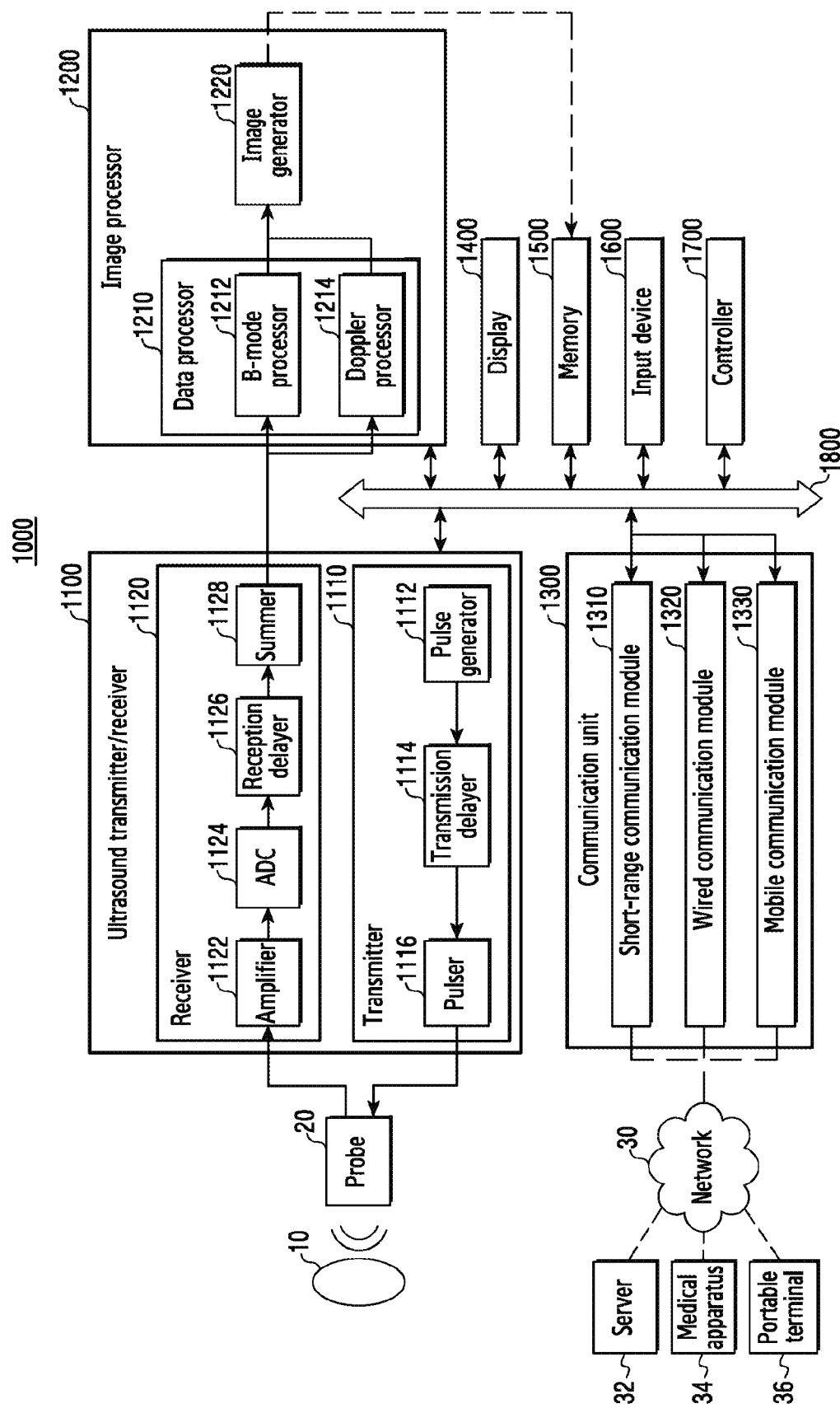
FIG. 1 is a block diagram illustrating a configuration of an ultrasound imaging apparatus related to an embodiment of the disclosure.

Hereinafter, embodiments of the disclosure will be described in detail with reference to the accompanying drawings so that they can be easily practiced by those having ordinary knowledge in the technical field to which the disclosure pertains. However, the disclosure may be implemented in various different forms, and is not limited to the embodiments described herein. Also, parts irrelevant to the disclosure are omitted in the drawings to make the disclosure clear, and the same reference numerals are designated to the same or similar elements throughout the specification.

The terms used herein will be selected in view of functions in the disclosure and among general terms currently widely used as much as possible. However, the meanings thereof may vary according to the intention of those skilled in the art, a precedent, the advent of new technology, or the like. Also, in a particular case, a term selected by the applicant as desired may be used, in which case the meaning thereof will be described in detail in the corresponding part of the description of the disclosure. Therefore, the terms used herein should be defined based on the meanings of the terms and the disclosure throughout this specification, not simply based on the names of the terms.

Throughout this specification, when it is described that an element is "connected" to another element, the first element may not only be "directly connected" to the second element, but may also be "electrically connected" to the second element through a third element. Also, throughout this specification, when it is described that a certain unit "includes" a certain element, this means that the unit may further include any other element rather than exclude the any other element unless otherwise described. Expressions such as "at least one of a, b, and c" should be understood as including only a, only b, only c, both a and b, both a and c, both b and c, all of a, b, and c, or other variations of thereof.

Throughout this specification, the term "ultrasound image" refers to an image of a subject acquired using ultrasound waves. Also, a subject may include a human, an animal, or a part of a human or an animal. For example, the subject may include at least one of organs, such as the liver, the heart, the womb, the brain, a breast, and the abdomen, and a blood vessel. Further, the subject may be a phantom. The phantom may refer to a material which approximates the density and effective atomic number of a living organism or the volume thereof. For example, the phantom may be a spherical phantom having characteristics similar to those of the human body.

Further, throughout this specification, a "user" may refer to a medical professional, such as a doctor, a nurse, a sonographer, a medical laboratory technologist, and a medical imaging expert, and a technician who repairs a medical apparatus, but the user is not limited thereto.

Hereinafter, embodiments of the disclosure will be described in detail with reference to the accompanying drawings.

FIG. 1 is a block diagram illustrating a configuration of an ultrasound imaging apparatus 1000 related to an embodiment of the disclosure.

The ultrasound imaging apparatus 1000 according to an embodiment of the disclosure may include a probe 20, an ultrasound transmitter/receiver 1100, an image processor 1200, a communication unit 1300, a display 1400, a memory 1500, an input device 1600, and a controller 1700, and the above-described multiple elements may be connected to each other through a bus 1800.

The ultrasound imaging apparatus 1000 may be implemented with a medical imaging cart, or as a portable type ultrasound system. Examples of portable ultrasound imaging apparatuses may include a Picture Archiving and Communications System (PACS) viewer, a smartphone, a laptop computer, a Personal Digital Assistant (PDA), a tablet Personal Computer (PC), a desktop computer, and the like. However, embodiments of the disclosure are not limited thereto.

The probe 20 transmits an ultrasound signal to a subject 10, according to a driving signal applied by the ultrasound transmitter/receiver 1100, and receives an echo signal reflected from the subject 10. The probe 20 includes multiple transducers that oscillate according to electrical signals delivered thereto and generate ultrasound waves which are acoustic energy. Also, the probe 20 may be connected to a main body of the ultrasound imaging apparatus 1000 by wire, or wirelessly. According to embodiments of the disclosure, the ultrasound imaging apparatus 1000 may include multiple probes 20.

A transmitter 1110 supplies a driving signal to the probe 20, and includes a pulse generator 1112, a transmission delayer 1114, and a pulser 1116. The pulse generator 1112 generates pulses for forming transmission ultrasound waves according to a predetermined Pulse Repetition Frequency (PRF), and the transmission delayer 1114 applies, to the pulses, a delay time for determining transmission directionality. Pulses, to which a delay time is applied, respectively correspond to multiple piezoelectric vibrators included in the probe 20. The pulser 1116 applies a driving signal (or a driving pulse) to the probe 20 at a timing corresponding to each pulse to which a delay time is applied.

A receiver 1120 generates ultrasound data by processing echo signals received from the probe 20, and may include an amplifier 1122, an Analog-to-Digital Converter (ADC) 1124, a reception delayer 1126, and a summer 1128. The amplifier 1122 amplifies an echo signal in each channel, and the ADC 1124 performs analog-to-digital conversion on the amplified echo signal. The reception delayer 1126 applies, to the digital-converted echo signals, delay times for determining reception directionality, and the summer 1128 generates ultrasound data by summing the echo signals processed by the reception delayer 1126. Meanwhile, according to embodiments of the disclosure, the receiver 1120 may not include the amplifier 1122. That is, when the sensitivity of the probe 20 or the capability of the Analog-to-Digital Converter (ADC) 1124 to process bits is enhanced, the amplifier 1122 may be omitted, and is optional.

The image processor 1200 generates an ultrasound image by scan-converting ultrasound data generated by the ultrasound transmitter/receiver 1100. Meanwhile, an ultrasound image that is produced by the image processor and image generator may include not only a gray-scale ultrasound image obtained by scanning a subject in an Amplitude (A) mode, a Brightness (B) mode, and a Motion (M) mode, but also a Doppler image representing a moving subject by using a Doppler effect. The Doppler image may include a blood flow Doppler image (or referred to as a "color Doppler image") showing the flow of blood, a tissue Doppler image showing the movement of a tissue, and a spectral Doppler image representing the moving speed of a subject as a waveform.

A B-mode processor 1212 included in a data processor 1210 extracts a B-mode component from ultrasound data and processes the extracted B-mode component. An image generator 1220 may generate an ultrasound image, which represents a signal intensity as brightness, on the basis of the B-mode component extracted by the B-mode processor 1212.

Similarly, a Doppler processor 1214 included in the data processor 1210 may extract a Doppler component from ultrasound data, and the image generator 1220 may generate a Doppler image, which represents the movement of a subject as a color or waveform, on the basis of the extracted Doppler component.

The image generator 1220 according to an embodiment of the disclosure may generate a three-dimensional (3D) ultrasound image by volume-rendering volume data, and may generate an elasticity image showing the degree of deformation of the subject 10 due to pressure. Further, the image generator 1220 may control the display 1400 to display and/or overlay various pieces of additional information on an ultrasound image, such as text and graphics. Also, the generated ultrasound image may be stored in the memory 1500.

The display 1400 displays and outputs the generated ultrasound image. The display 1400 may display and output not only an ultrasound image but may also display and/or overlay various pieces of information processed by the ultrasound imaging apparatus 1000 on a screen through a Graphical User Interface (GUI). Meanwhile, the ultrasound imaging apparatus 1000 may include two or more displays 1400 according to embodiments of the disclosure.

The communication unit 1300 can be connected to a network 30 by at least one wire, or wirelessly, and communicates with an external device or a server. The communication unit 1300 may exchange data with a hospital server or another medical apparatus in a hospital that is connected through a Picture Archiving and Communications System (PACS). Also, the communication unit 1300 may perform data communication according to a Digital Imaging and Communications in Medicine (DICOM) standard.

The communication unit 1300 may transmit or receive data related to diagnosis of the subject 10 (e.g., an ultrasound image, ultrasound data, and Doppler data of the subject 10) through the network 30, and may also transmit or receive medical images taken by other medical apparatuses, such as a CT apparatus, an MRI apparatus, an X-ray apparatus, and the like. The communication unit 1300 may receive, from a server 32, information on a diagnosis history or a treatment schedule of a patient which can be utilized to diagnose the patient (i.e., the subject 10). The communication unit 1300 may perform data communication with the server 32 or a medical apparatus 34 in a hospital as well as a portable terminal 36 of a doctor or patient. The portable terminal 36 could be a smartphone, an electronic tablet, a smart watch, a laptop computer, or another type of portable electronic device that can receive and display information.

The communication unit 1300 is connected to the network 30 by at least one wire, or wirelessly, and may exchange data with the server 32, the medical apparatus 34, or the portable terminal 36. The communication unit 1300 may include at least one element that enables communication with an external device, and may include, for example, a short-range communication module 1310, a wired communication module 1320, and a mobile communication module 1330. Alternatively, the communication unit 1300 could include just one of these modules, or two of these modules.

The short-range communication module 1310 is a module for short-distance communication within a predetermined distance. Examples of short-range communication technology according to an embodiment of the disclosure may include a wireless Local Area Network (LAN), Wi-Fi, Bluetooth, ZigBee, Wi-Fi Direct (WFD), Ultra-WideBand (UWB), Infrared Data Association (IrDA), Bluetooth Low Energy (BLE), and Near Field Communication (NFC), but are not limited thereto. Thus the short-range communication module 1310 may include communication circuitry for performing short-distance communication.

The wired communication module 1320 is a module for performing communication by using an electrical signal or an optical signal. Wired communication according to an embodiment of the disclosure may be performed using a twisted-pair cable, a coaxial cable, an optical fiber cable, an Ethernet cable, or the like. Thus the wired communication module 1320 may include communication circuitry for performing wired communication.

The mobile communication module 1330 transmits/receives a wireless signal to/from at least one of a base station, an external terminal, and a server over a mobile communication network. Here, the wireless signal may include a voice call signal, a video call signal, or various types of data according to transmission/reception of a text/multimedia message. Thus the mobile communication module 1330 may include communication circuitry for performing wireless communication.

The memory 1500 stores various pieces of information processed by the ultrasound imaging apparatus 1000. For example, the memory 1500 may store medical data, such as input/output ultrasound data and ultrasound images, related to the diagnosis of a subject, and may also store an algorithm or a program which is executed in the ultrasound imaging apparatus 1000.

The memory 1500 may be implemented by various types of storage media such as a flash memory, a hard disk, an Electrically Erasable Programmable Read-Only Memory (EEPROM), and the like. Also, the ultrasound imaging apparatus 1000 may be connected to a web-based storage or a cloud server, which performs a storage function of the memory 1500 over the web, through a network.

The input device 1600 is a device by which a user inputs data for controlling the ultrasound imaging apparatus 1000. The input device 1600 may include hardware elements, such as a keypad, a mouse, a touch pad, a touch screen on a display, a trackball, a jog switch, and the like, but is not limited thereto. The input device 1600 may further include various input elements, such as an electrocardiogram (ECG) measurement module, a breath measurement module, a voice recognition sensor (i.e., a microphone), a gesture recognition sensor (i.e., a camera), a fingerprint recognition sensor, an iris recognition sensor, a depth sensor, a distance sensor, and the like.

The controller 1700 controls an overall operation of the ultrasound imaging apparatus 1000. That is, the controller 1700 may control operations among the probe 20, the ultrasound transmitter/receiver 1100, the image processor 1200, the communication unit 1300, the display 1400, the memory 1500, and the input device 1600 which are illustrated in FIG. 1.

The controller 1700 may control an ultrasound signal to be transmitted to the subject 10 through the probe 20 according to a command that the user has input, and may control an output of the transmitted ultrasound signal.

The controller 1700 may include a memory that stores a program, which performs the above-described operations and operations described below, and a processor that executes a stored program.

The controller 1700 may include a single processor or multiple processors, and in the latter case, the multiple processors may be integrated into one chip, or may be physically separated from each other.

Some or all of the probe 20, the ultrasound transmitter/receiver 1100, the image processor 1200, the communication unit 1300, the display 1400, the memory 1500, the input device 1600, and the controller 1700 may be operated by a software module, but are not limited thereto. Some of the above-described elements may be operated by a hardware module. Also, at least some, or in some cases all, of the ultrasound transmitter/receiver 1100, the image processor 1200, and the communication unit 1300 may be included in the controller 1700.

The memory 1500 may store a learning network model (or a trained model).

A learning network model may be designed to simulate the structure of a human brain on a computer.

For example, a learning network model may include multiple network nodes which have weights and simulate neurons of a neural network of the human brain. Multiple network nodes may form a connection relationship therebetween so as to simulate the synaptic activity of neurons which exchange signals through synapses.

The learning network model may include, for example, an AI neural-network model or a deep-learning network model evolved from a neural-network model. In the deep-learning network model, multiple network nodes may exchange data according to a convolution connection relationship while being located at different depths (or different layers).

A learning network model may be implemented by, for example, a software module. When a learning network model is implemented by a software module (e.g., a program module including instructions), the learning network model may be stored in a computer-readable recording medium. In this case, the computer-readable recording medium may become at least part of the memory 1500.

As another example, a learning network model may be integrated in the form of a hardware chip and may become a part of the above-described controller 1700. For example, the learning network model may be manufactured in the form of a dedicated hardware chip for AI, or may be manufactured as a part of an existing general-purpose processor (e.g., a Central Processing Unit (CPU) or an application processor) or as a part of a dedicated graphics processor (e.g., a Graphics Processing Unit (GPU)).

As still another example, a learning network model may be stored in the form of a software module or integrated with a hardware chip, or may be located at an AI cloud server 32.

In this case, the ultrasound imaging apparatus 1000 may transmit an ultrasound image to the server 32 through the communication unit 1300. The server 32 may be an AI cloud server. An ultrasound image may be, for example, an image obtained by manipulation/movement of the ultrasound imaging apparatus 1000 over the subject, according to a protocol by a sonographer.

The AI cloud server 32 may input an ultrasound image, which has been received from the ultrasound imaging apparatus 1000, into the learning network model to analyze the ultrasound image, and may transmit, to the ultrasound imaging apparatus 1000, information on whether the protocol has been followed and whether there is a need for additional imaging.

When a learning network model located at the AI cloud server 32 is implemented by a software module, the learning network model may be stored in a computer-readable recording medium. In this case, the computer-readable recording medium may be a memory (not illustrated) of the AI cloud server 32.

A learning network model may be generated by the AI cloud server 32. The AI cloud server 32 may be, for example, a server operated by a manufacturer of the ultrasound imaging apparatus 1000, a server operated by a manager of the ultrasound imaging apparatus 1000, or a server that the manufacturer or manager entrusts or lends to a third party. The AI cloud server 32 may only generate or update a learning network model, or may receive an ultrasound image from the ultrasound imaging apparatus 1000, and may provide a result of analysis of the received ultrasound image by using the learning network model.

The AI cloud server 32 may teach a learning network model by using learning data. The learning data may be, for example, patient information of various patients. The patient information may include the ages, genders, and names of diseases of patients, and medical image information according to the same. The medical image information may include an ultrasound image, an X-ray image, an MRI image, and a CT image.

Learning data may be collected from a hospital or a doctor by the manufacturer or manager of the ultrasound imaging apparatus 1000, or a result obtained using a learning network model by the ultrasound imaging apparatus 1000 may be reused as learning data.

A learning network model may be updated periodically or aperiodically. A case where the learning network model is aperiodically updated may be, for example, a case where a manager makes a request or the volume of collected learning data is greater than or equal to a predetermined value.

According to various embodiments of the disclosure, a process for generating a learning network model may be directly performed by the ultrasound imaging apparatus 1000. That is, the ultrasound imaging apparatus 1000 may teach and update a learning network model, and may even analyze an ultrasound image by using the learning network model.

Also, the AI cloud server 32 may include multiple servers. The AI cloud server 32 may include a system that stores and processes data by using resources of various apparatuses (e.g., a server, a client, etc.) interconnected in an Internet environment.

According to an embodiment of the disclosure, a learning network model may be configured to estimate an optimal diagnostic protocol and an image according to the same.

Here, the configuration of a learning network model with the above-described objectives may imply that the learning network model is taught not as a general learning network model capable of coping with various cases but for particular objectives and thus, an inside of the learning network model is implemented to meet the above-described objectives.

Figure 2:
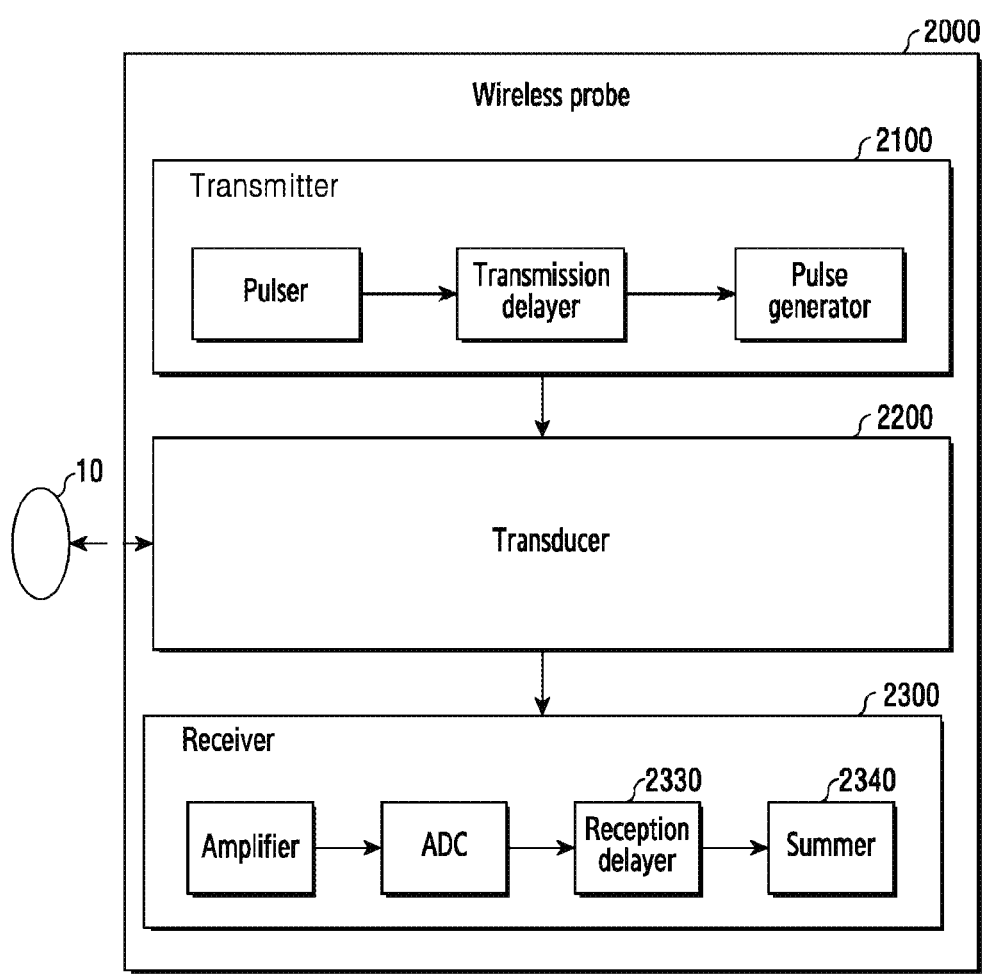
FIG. 2 is a block diagram illustrating a configuration of a wireless probe related to an embodiment of the disclosure.

FIG. 2 is a block diagram illustrating a configuration of a wireless probe 2000 related to an embodiment of the disclosure.

The wireless probe 2000 may include multiple transducers as described above, even though only one transducer is shown in FIG. 2, and may include some or all of the elements of the ultrasound transmitter/receiver 1100 illustrated in FIG. 1 according to embodiments of the disclosure.

The wireless probe 2000 according to the embodiment illustrated in FIG. 2 includes a transmitter 2100, a transducer 2200, and a receiver 2300. A description of each of the transmitter 2100, the transducer 2200, and the receiver 2300 has been set forth above with reference to FIG. 1. Accordingly, a detailed description thereof will be omitted. Meanwhile, according to embodiments of the disclosure, the wireless probe 2000 may include one of a reception delayer 2330 and a summer 2340, or both, but these components are optional and may be omitted in certain embodiments.

The wireless probe 2000 may transmit an ultrasound signal to the subject 10 and receive an echo signal from the subject 10, and may generate ultrasound data to wirelessly (or via a wired connection) transmit the generated ultrasound data to the ultrasound imaging apparatus 1000 illustrated in FIG. 1.

Figure 3:
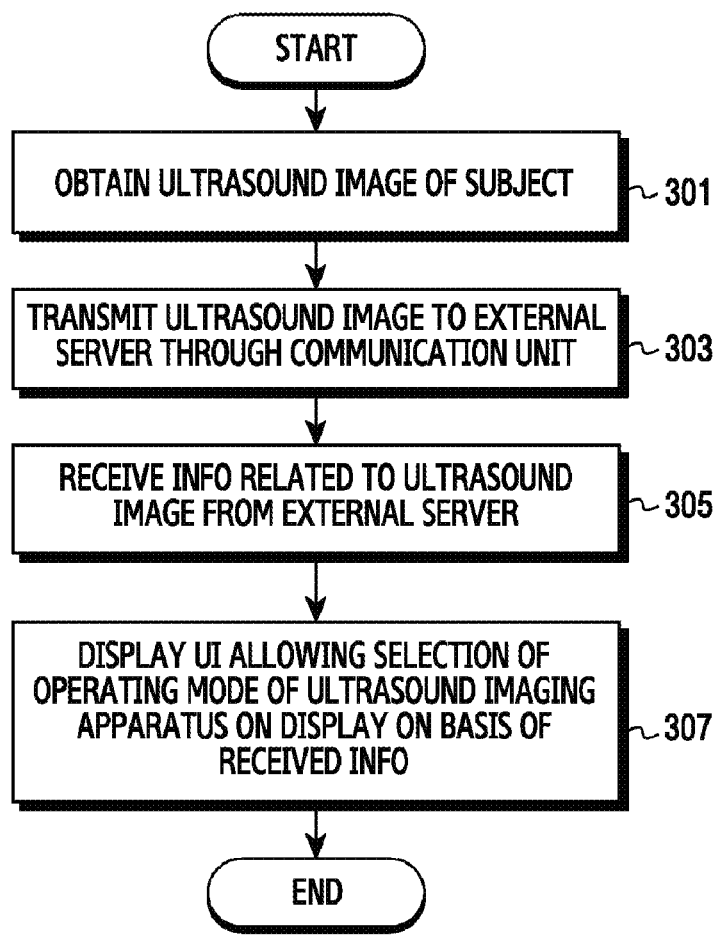
FIG. 3 is a flowchart illustrating a control method of an ultrasound imaging apparatus related to an embodiment of the disclosure.

FIG. 3 is a flowchart illustrating a control method of an ultrasound imaging apparatus related to an embodiment of the disclosure.

Referring to FIG. 3, in operation 301, the ultrasound imaging apparatus (e.g., the ultrasound imaging apparatus 1000 of FIG. 1) may obtain an ultrasound image of a subject by using ultrasound imaging. When a sonographer manipulates the ultrasound imaging apparatus according to a protocol, the ultrasound imaging apparatus may perform ultrasonography by irradiating an ultrasound wave to the subject, and may obtain an ultrasound image of the subject. The protocol may include information on an area of the subject which needs to be imaged based on a disease of the subject, a relevant imaging method, and/or a relevant landmark. The landmark may signify a particular pattern and shape used to image a particular disease in an ultrasound image.

In operation 303, the ultrasound imaging apparatus may transmit the obtained ultrasound image to an external server (e.g., the server 32) through a communication unit (e.g., the communication unit 1300). The external server may be, for example, an AI cloud server. The external server may be a server operated by a manufacturer of the ultrasound imaging apparatus, or a server operated by a hospital. Since an AI cloud server is the same as described above with reference to FIG. 1, a detailed description thereof will be omitted.

According to another embodiment, an AI cloud server may be connected to a separate server operated by a hospital through a communication channel, and the AI cloud server may receive subject information. The subject information may include prescription details that a doctor has issued for a subject.

The AI cloud server may generate a protocol optimized for the subject, by applying, to a learning network model, the subject information and/or the ultrasound image received from the ultrasound imaging apparatus.

According to the protocol optimized for the subject, the AI cloud server may determine an area to be imaged, the number of images, an imaging direction, the type of ultrasound probe, an imaging depth, the size of an area to be imaged, an annotation mark, and whether the annotation mark coincides with the area to be imaged.

The AI cloud server may determine whether the sonographer has followed the protocol, on the basis of the generated protocol, and may transmit feedback concerning a result of the determination to the ultrasound imaging apparatus in the form of a notification message that can be read by the sonographer.

The AI cloud server may check whether a quantitative measurement list has been performed with respect to the ultrasound image, and may determine whether the ultrasound image obtained by the ultrasound imaging apparatus is appropriate for reading. For example, when a tumor has been found in the ultrasound image, the AI cloud server may determine whether the size of the tumor has been measured.

When it is determined, through the analysis of an ultrasound image using a learning network model, that an additional examination (e.g., a contrast medium examination, shear wave measurement, Doppler measurement, etc.) is required beyond a simple B-mode examination, the AI cloud server may transmit information on this determination to at least one of the ultrasound imaging apparatus, a radiologist, and a workstation of a clinician who has indicated an ultrasound prescription. The information on this determination can then be displayed.

The AI cloud server may determine, through the analysis of an ultrasound image using the learning network model, whether the ultrasound image has an appropriate resolution. When it is determined that the ultrasound image has an inappropriate resolution or has a resolution difficult to read, the AI cloud server may transmit, to the ultrasound imaging apparatus, information related to the inappropriateness of the ultrasound image for reading. The information on this determination can then be displayed.

As described above, the AI cloud server may apply the ultrasound image received from the ultrasound imaging apparatus to the learning network model, and may determine whether the ultrasound image is appropriate for reading, and may generate information related to the ultrasound image on the basis of a result of the determination.

In operation 305, the ultrasound imaging apparatus may receive the information related to the ultrasound image from the external server/AI cloud server. The information related to the ultrasound image may include information on a protocol generated by the AI cloud server, whether the ultrasound image is appropriate for reading, a resolution of the ultrasound image, whether an additional ultrasound image should be taken, and/or whether to have an additional examination.

In operation 307, the ultrasound imaging apparatus may display a User Interface (UI), which enables a user to select an operating mode of the ultrasound imaging apparatus, on a display (e.g., the display 1400) on the basis of the information received from the AI cloud server. When the received information includes information on an additionally-required ultrasound image, the ultrasound imaging apparatus may display the UI, which enables the user to select an operating mode of the ultrasound imaging apparatus, on the display. For example, when the ultrasound image is determined to include a tumor as a result of the analysis of the ultrasound image through the learning network model, the AI cloud server may transmit information, which requests the user to perform shear wave or Doppler imaging, to the ultrasound imaging apparatus. The ultrasound imaging apparatus may then display a UI with a shear wave mode button and a Doppler mode button on the display according to the information.

The UI may be, for example, a button-shaped graphic object that enables the user to select a shear wave mode or a Doppler mode. The ultrasound imaging apparatus may receive a user input for selecting the UI displayed on the display, and may operate in the shear wave mode or Doppler mode on the basis of the received user input. For example, when the user selects a Doppler mode display button from among the buttons displayed on the display, the ultrasound imaging apparatus may operate in the Doppler mode. When the user selects a shear wave mode display button, the ultrasound imaging apparatus may operate in the shear wave mode. When the display is a touch display, the user may operate the ultrasound imaging apparatus in the shear wave mode or Doppler mode by touching a button displayed on the display.

When a tumor is identified in the ultrasound image on the basis of the information, the ultrasound imaging apparatus may display a UI, which requests a size measurement of the tumor, on the display.

In some embodiments, a learning network model may be stored in the ultrasound imaging apparatus. In this case, the ultrasound imaging apparatus may acquire information on a subject, and may input an ultrasound image to the learning network model to analyze the ultrasound image. The learning network model may be stored in a memory in the form of a program, or may be implemented by a separate dedicated hardware processor. When the learning network model is stored within the ultrasound imaging apparatus, the learning network model may be updated periodically or aperiodically through the communication unit 1300. That is, the learning network model may be updated by receiving updates from an external server such as server 32.

The ultrasound imaging apparatus may display a UI, which enables the user to select an operating mode of the ultrasound imaging apparatus, on the display on the basis of a result of the analysis, may receive a user input for selecting one operating mode by using the UI, and may operate in the selected operating mode on the basis of the received user input. The ultrasound imaging apparatus may obtain a new ultrasound image according to the selected operating mode. The UI may be displayed on the display 1400.

Figure 4:
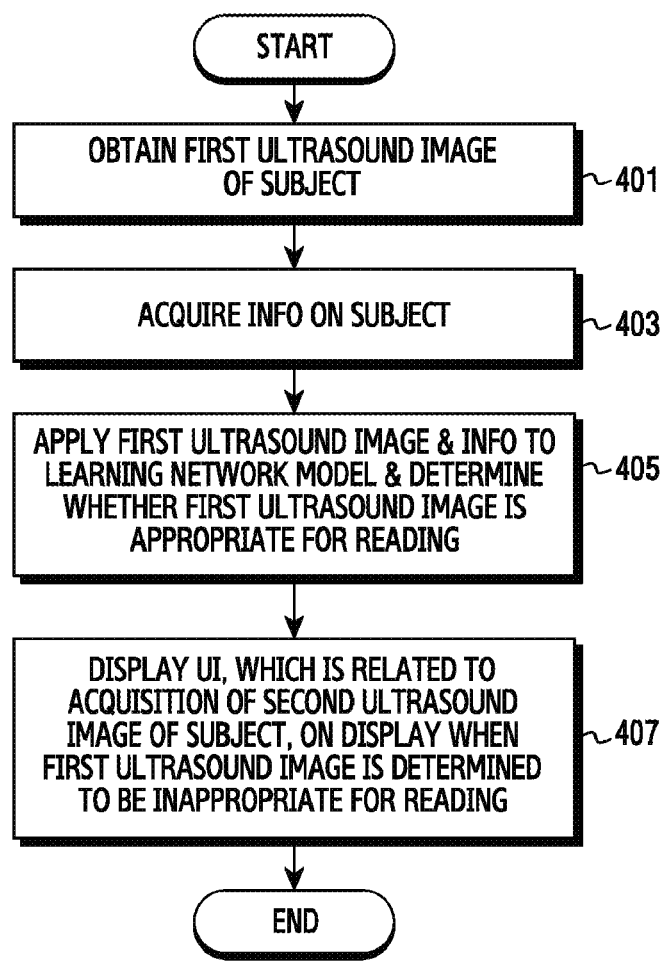
FIG. 4 is a flowchart illustrating a control method of another ultrasound imaging apparatus related to an embodiment of the disclosure.

FIG. 4 is a flowchart illustrating a control method of another ultrasound imaging apparatus related to an embodiment of the disclosure.

In operation 401, the ultrasound imaging apparatus (e.g., the ultrasound imaging apparatus 1000) may obtain a first ultrasound image of a subject by using ultrasound imaging. When a sonographer manipulates the ultrasound imaging apparatus according to a protocol for the subject, the ultrasound imaging apparatus may perform ultrasonography by irradiating an ultrasound wave to the subject, and may obtain the first ultrasound image of the subject.

In operation 403, the ultrasound imaging apparatus may acquire information on the subject. The ultrasound imaging apparatus may be connected to a medical information management server, which is operated by a hospital, through wired or wireless communication channels, and may receive medical information of the subject from the medical information management server. The medical information of the subject may include prescription details that a doctor has issued for the subject, or information such as the height, weight, sex, and disease condition of the patient.

In operation 405, the ultrasound imaging apparatus may apply the ultrasound image and the medical information to a learning network model and may determine whether the ultrasound image is appropriate for reading. The learning network model may be stored within the ultrasound imaging apparatus, and may be stored in a memory (e.g., the memory 1500) in the form of a program, or may be implemented by a separate dedicated hardware processor. When the learning network model is stored within the ultrasound imaging apparatus, the learning network model may be updated periodically or aperiodically through a communication unit (e.g., the communication unit 1300), by receiving updates from an external server such as server 32. The ultrasound imaging apparatus may generate a protocol for the subject by applying, to the learning network model, the obtained first ultrasound image and the information on the subject. The ultrasound imaging apparatus may determine whether the first ultrasound image is appropriate for reading, according to the generated protocol. A detailed description thereof is the same as described above with reference to FIG. 3, and thus will be omitted.

In operation 407, when the first ultrasound image is determined to be inappropriate for reading, the ultrasound imaging apparatus may display a UI, which is related to the acquisition of a second ultrasound image of the subject, on a display (e.g., the display 1400). The UI may include, for example, at least one button that enables a user to select an operating mode of the ultrasound imaging apparatus.

For example, in order to determine the appropriateness of the first ultrasound image for reading, the ultrasound imaging apparatus may detect a landmark in the first ultrasound image according to an arithmetic operation which is based on a connection relationship between multiple network nodes, which configure a learning network model, and respective weights of the multiple network nodes.

When the first ultrasound image is determined to be appropriate for reading, the ultrasound imaging apparatus may transmit the first ultrasound image to an external electronic apparatus through a communication unit. The external electronic apparatus may be, for example, a smartphone, tablet, or workstation of a doctor.

The ultrasound imaging apparatus may receive, from the external electronic apparatus of the doctor, a reply as to whether the first ultrasound image is appropriate for reading. For example, the ultrasound imaging apparatus may transmit an image, which has been determined to be appropriate for reading, to an external electronic apparatus through a communication unit, and when receiving, from the external electronic apparatus, a reply indicating that the image is appropriate for reading, may finally determine that the image is an appropriate image. In contrast, when receiving, from the external electronic apparatus, a reply indicating that the image is inappropriate for reading (e.g., when a doctor inputs a reply indicating that the received image is inappropriate for reading), the ultrasound imaging apparatus may display an interface, which requests re-imaging (or reexamination), on the display. According to some embodiments of the disclosure, when transmitting a reply indicating that the image received is inappropriate for reading, the external electronic apparatus may transmit information on the imaging together with the reply based on the request of a user (e.g., a doctor).

According to some embodiments of the disclosure, in order to determine the appropriateness of a first ultrasound image for reading, the ultrasound imaging apparatus may detect a particular shape in the first ultrasound image by using a learning network model. The particular shape may be, for example, a tumor. According to the detection of the particular shape, the ultrasound imaging apparatus may display a UI, which enables the user to select an operating mode of the ultrasound imaging apparatus, on the display. An example thereof is the same as described above with reference to FIG. 3, and thus, a detailed description thereof will be omitted.

FIG. 5 is a view illustrating an example of a plurality of ultrasound image prescription codes that can be issued by a doctor.

An ultrasound imaging apparatus (e.g., the ultrasound imaging apparatus 1000) may store a prescription code list 501. When a doctor has input a prescription code into an external electronic apparatus, the input prescription code may be transmitted to ultrasound imaging apparatus.

FIG. 6A is a view illustrating an example of a protocol related to an embodiment of the disclosure.

Referring to FIG. 6A, an ultrasound imaging apparatus (e.g., the ultrasound imaging apparatus 1000) may display a protocol 601, which corresponds to a prescription code received through a communication unit (e.g., the communication unit 1300), on a display (e.g., the display 1400). A sonographer may manipulate the ultrasound imaging apparatus with reference to the protocol 601 displayed on the display and may obtain an ultrasound image according to the protocol 601.

Figure 6B:
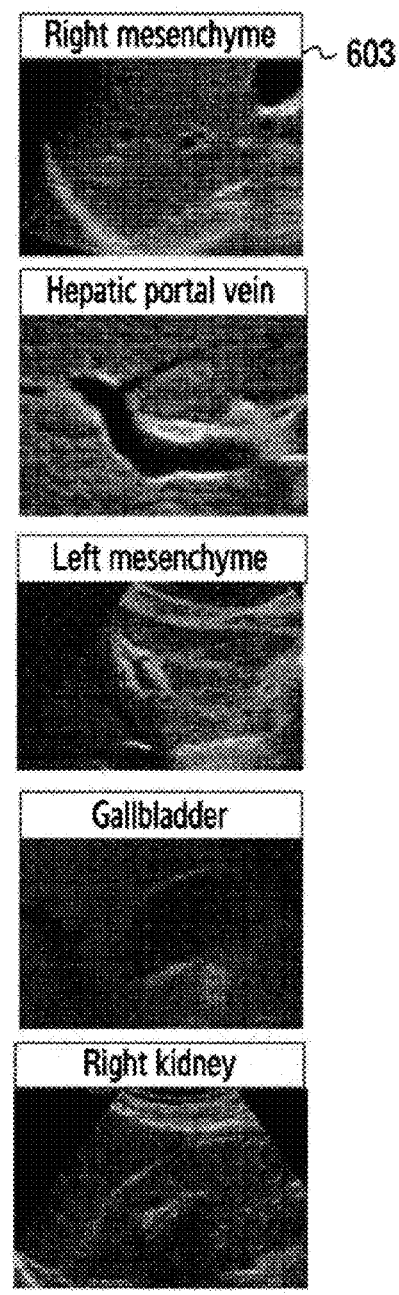
FIG. 6B is a view illustrating an example of an ultrasound image taken by an ultrasound imaging apparatus related to an embodiment of the disclosure.

FIG. 6B is a view illustrating an example of a series of ultrasound images taken by an ultrasound imaging apparatus related to an embodiment of the disclosure.

FIG. 6B illustrates a series of ultrasound images 603 of a particular area of a subject. The ultrasound images 603 may include one or more ultrasound images of the particular area of the subject. For example, examples of the ultrasound image 603 may include an ultrasound image obtained by imaging the right mesenchyme, an ultrasound image obtained by imaging the hepatic portal vein, an ultrasound image obtained by imaging the left mesenchyme, an ultrasound image obtained by imaging the gallbladder, and an ultrasound image obtained by imaging the right kidney.

However, this configuration is only an example, and thus, embodiments of the disclosure are not limited thereto. That is, other areas of the subject could certainly be imaged.

Figure 7:
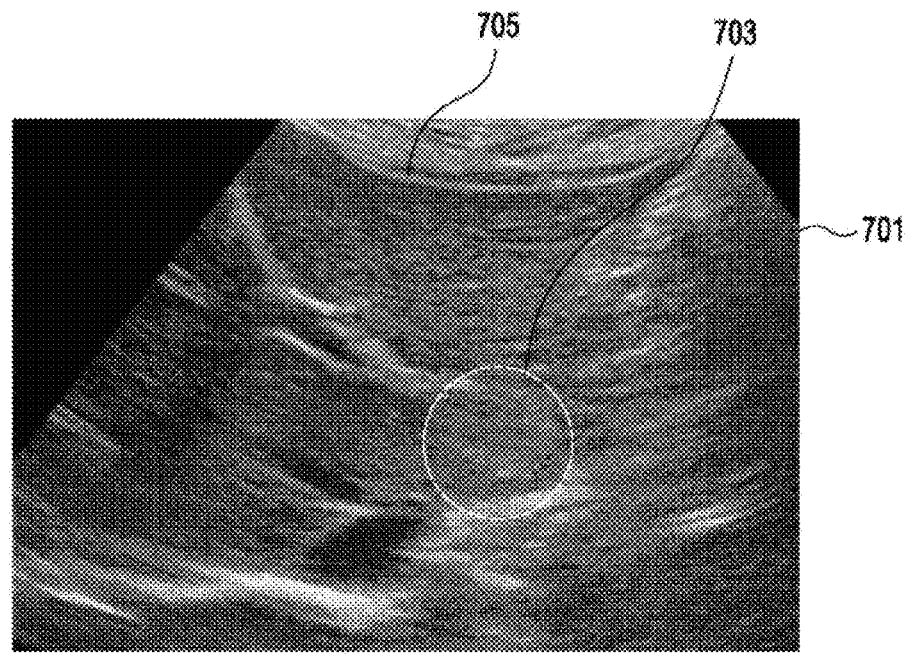
FIG. 7 is a view illustrating an example of applying, to a learning network model, and analyzing an image taken by an ultrasound imaging apparatus related to an embodiment of the disclosure.

FIG. 7 is a view illustrating an example of applying, to a learning network model, and analyzing an image taken by an ultrasound imaging apparatus related to an embodiment of the disclosure.

The learning network model may be stored within the ultrasound imaging apparatus (e.g., the ultrasound imaging apparatus 1000), or may be stored in an AI cloud server (e.g., the server 32).

FIG. 7 illustrates an ultrasound image 701. The ultrasound image 701 may include particular shapes 703 and 705. The learning network model may identify the particular shapes 703 and 705 by analyzing the ultrasound image 701, and may provide the ultrasound imaging apparatus with information on the particular identified shapes 703 and 705 and information on a method for subsequently processing the particular identified shapes 703 and 705.

For example, when the particular shape 703 is identified as a tumor by using the learning network model, the learning network model may transmit information on the shape/tumor 703 to the ultrasound imaging apparatus. The ultrasound imaging apparatus may display a message, which requests a size measurement of the tumor on the basis of the received information, on the display, or may operate in a size measurement mode. Alternatively, the learning network model could determine that additional imaging of the tumor is needed, and transmit information indicating that additional imaging of the tumor is needed to the ultrasound imaging apparatus.

Also, the ultrasound imaging apparatus may display a button, which enables a user to operate the ultrasound imaging apparatus in a shear wave mode or Doppler mode, on the display 1400 on the basis of the received information.

Figure 8:
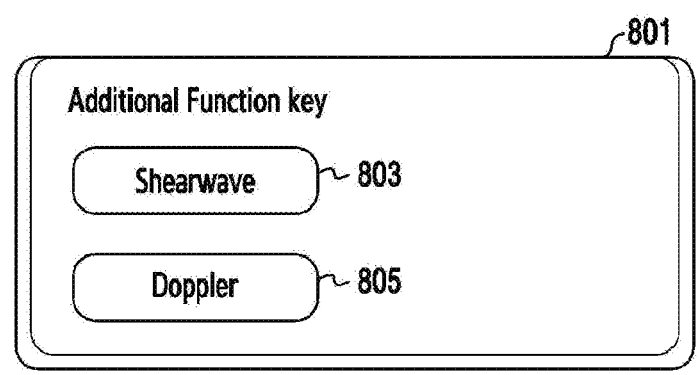
FIG. 8 is a view illustrating an example of a user interface displayed on a display of an ultrasound imaging apparatus according to an embodiment of the disclosure.

FIG. 8 is a view illustrating an example of a UI displayed on a display of an ultrasound imaging apparatus according to an embodiment of the disclosure.

FIG. 8 illustrates a display 801 (e.g., the display 1400) and UI buttons 803 and 805 of the ultrasound imaging apparatus (e.g., the ultrasound imaging apparatus 1000).

The ultrasound imaging apparatus may display the UI buttons 803 and 805 on the display 801 on the basis of information transmitted by an AI cloud server (e.g., the server 32).

The UI buttons 803 and 805 may be, for example, button-shaped graphic objects. When the display 801 is implemented by a touch screen, the ultrasound imaging apparatus may receive a user input of a touch applied to the UI button 803, and the ultrasound imaging apparatus may operate in a shear wave mode according to the received user input. Alternatively, the ultrasound imaging apparatus may receive a user input of a touch applied to the UI button 805, and may operate in a Doppler mode according to the received user input.

Figure 9A:
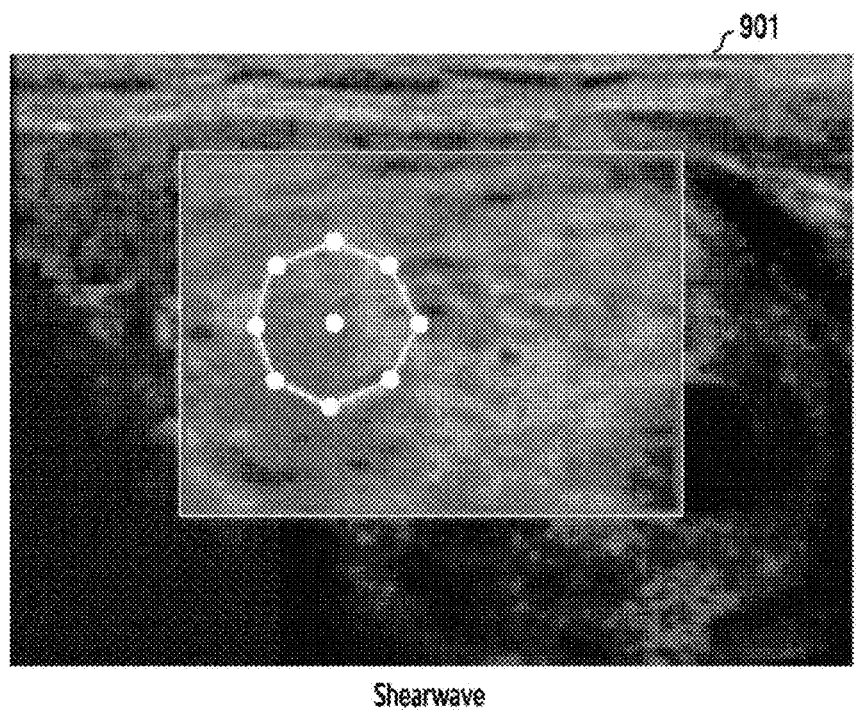
FIGS. 9A and 9B are views respectively illustrating examples of ultrasound images taken in a shear wave mode and a Doppler mode of an ultrasound imaging apparatus according to an embodiment of the disclosure.
Figure 9B:
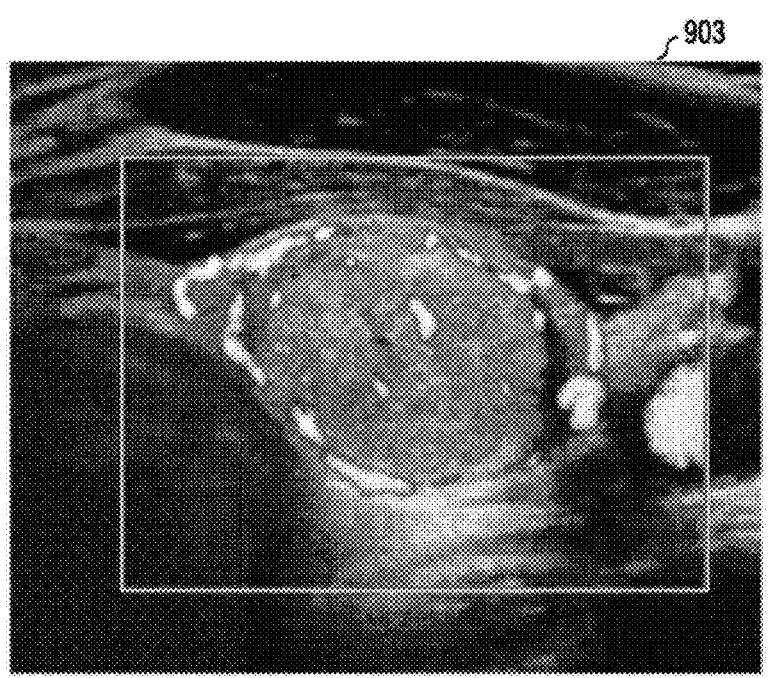

FIGS. 9A and 9B are views respectively illustrating examples of ultrasound images taken in a shear wave mode and a Doppler mode of an ultrasound imaging apparatus according to an embodiment of the disclosure.

FIG. 9A illustrates an example of the ultrasound image 901 taken by the ultrasound imaging apparatus (e.g., the ultrasound imaging apparatus 1000) operating in the shear wave mode.

When a user touches a shear wave mode button (reference numeral 803 of FIG. 8) displayed on a display (e.g., the display 1400 or 801) of the ultrasound imaging apparatus, the ultrasound imaging apparatus may operate in the shear wave mode and may take the ultrasound image 901.

FIG. 9B illustrates an example of the ultrasound image 903 taken by the ultrasound imaging apparatus operating in the Doppler mode.

When the user touches a Doppler mode button (reference numeral 805 of FIG. 8) displayed on the display of the ultrasound imaging apparatus, the ultrasound imaging apparatus may operate in the Doppler mode and may take the ultrasound image 903.

Figure 10A:
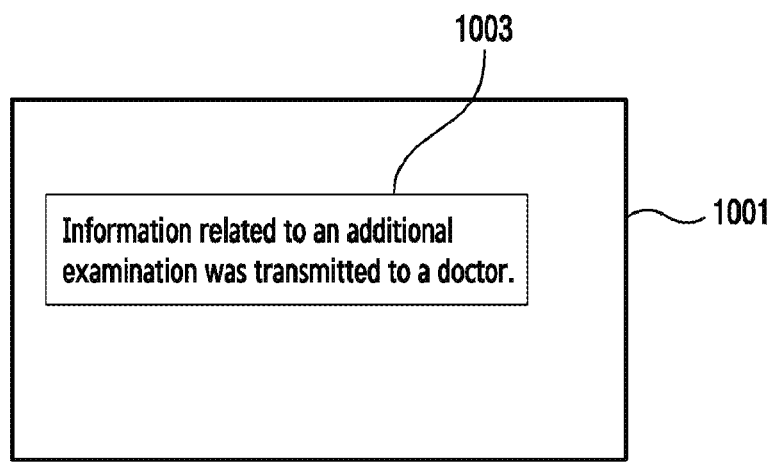
FIGS. 10A and 10B are views each illustrating an example of notification information displayed on a display of an ultrasound imaging apparatus according to an embodiment of the disclosure.
Figure 10B:
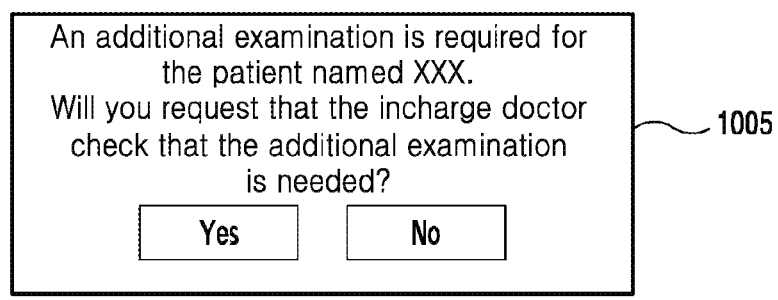

FIGS. 10A and 10B are views each illustrating an example of notification information displayed on a display of an ultrasound imaging apparatus according to an embodiment of the disclosure.

Referring to FIGS. 10A and 10B, the ultrasound imaging apparatus (e.g., the ultrasound imaging apparatus 1000) may display notification information 1003 on the display 1001 (e.g., the display 1400 or 801) on the basis of a result of the analysis of the ultrasound image through a learning network model. As described above, the learning network model may be stored in an external server, or may be stored within the ultrasound imaging apparatus.

When an additional examination is determined to be required as a result of the analysis of the ultrasound image by using the learning network model, the external server or ultrasound imaging apparatus may generate information on necessity for the additional examination and may provide the generated information to an operator (e.g., a sonographer) of the ultrasound imaging apparatus and an in-charge doctor. For example, when the learning network model is provided in the external server, the external server may transmit information on necessity for the additional examination to the ultrasound imaging apparatus and/or a designated external electronic apparatus (e.g., a workstation of an in-charge doctor, a desktop PC, a portable electronic apparatus (e.g., a smart phone or tablet), etc.). Also, the external server may transmit, to the ultrasound imaging apparatus, notification information 1003 that indicates that transmission of the information to the external electronic apparatus has occurred.

In some embodiments, when the ultrasound imaging apparatus includes a learning network model, the ultrasound imaging apparatus may transmit information on a necessity for an additional examination, to a designated external electronic apparatus (e.g., a workstation of an in-charge doctor, a desktop PC, a portable electronic apparatus (e.g., a smart phone or tablet), etc.).

When receiving, from an external server, notification information notifying of the transmission of the information to the in-charge doctor, the ultrasound imaging apparatus may display the notification information 1003 on the display 1001 as illustrated in FIG. 10A. Similarly, the ultrasound imaging apparatus may transmit the information to an external electronic apparatus, and then may display the notification information 1003 on the display 1001.

According to some embodiments of the disclosure, before transmitting the information, the ultrasound imaging apparatus may display, on the display, an interface (e.g., a pop-up window) that permits a user to select whether or not the information on necessity for an additional examination is transmitted to an external electronic apparatus. For example, as illustrated in FIG. 10B, the ultrasound imaging apparatus may display, on the display, a pop-up message 1005, such as "An additional examination is required for the patient named XXX. Will you request that the in-charge doctor check that the additional examination is needed?" When an operator (e.g., a sonographer) of the ultrasound imaging apparatus selects "Yes" through the pop-up message 1005, the ultrasound imaging apparatus may transmit, to an external electronic apparatus, the information on necessity for the additional examination. In contrast, when the operator (e.g., a sonographer) of the ultrasound imaging apparatus selects "No" through the pop-up message 1005, the ultrasound imaging apparatus may not transmit, to the external electronic apparatus, the information on necessity for the additional examination.

FIGS. 10C and 10D are views each illustrating an example of an interface displayed on a display of an external electronic apparatus according to an embodiment of the disclosure.

Referring to FIGS. 10C and 10D, the external electronic apparatus (e.g., a workstation of an in-charge doctor, a desktop PC, a portable electronic apparatus (e.g., a smart phone or tablet), etc.) having received the information on necessity for the additional examination, may notify a user of the external electronic apparatus (e.g., the in-charge doctor) of the reception of the information in various manners. For example, as illustrated in FIG. 10C, the external electronic apparatus may output a pop-up message 1007. This configuration is only an example, and thus, embodiments of the disclosure are not limited thereto. For example, the external electronic apparatus may notify a user of the external electronic apparatus (e.g., the in-charge doctor) of the reception of the information through the output of a sound effect, the generation of a vibration, the flickering of a light-emitting apparatus (e.g., Light-Emitting Diodes (LEDs)), the display of a designated icon (or indicator), and the like.

The in-charge doctor may transmit a reply as to whether the additional examination is to be performed, to the ultrasound imaging apparatus by using the pop-up message 1007. For example, when the selection of an approval item ("Yes") included in the pop-up message 1007 is detected, the external electronic apparatus may transmit, to the ultrasound imaging apparatus, a response signal for allowing the additional examination to be performed with the ultrasound imaging apparatus.

According to some embodiments of the disclosure, when the additional examination includes multiple additional examination items, if the approval item is selected, the external electronic apparatus may display the additional examination items (i.e., more than one examination item). For example, as illustrated in FIG. 10D, the external electronic apparatus may output a pop-up message 1009 including multiple selectable additional examination items. The in-charge doctor may select at least one additional examination item from among the additional examination items. The external electronic apparatus may then transmit the selected at least one additional examination item to the ultrasound imaging apparatus so that the sonographer can perform the at least one additional examination item. Although the pop-up message 1009 is illustrated as including a shear wave mode and a Doppler mode in FIG. 10D, this configuration is only an example, and thus, embodiments of the disclosure are not limited thereto.

In contrast, when the selection of a disapproval item ("No") included in the pop-up message 1007 is detected, the external electronic apparatus may transmit, to the ultrasound imaging apparatus, a response signal for not allowing the additional examination. That is, the external electronic apparatus may transmit information indicating that the additional examination should not be performed, and this information may be displayed on the ultrasound imaging apparatus.

Figure 10E:
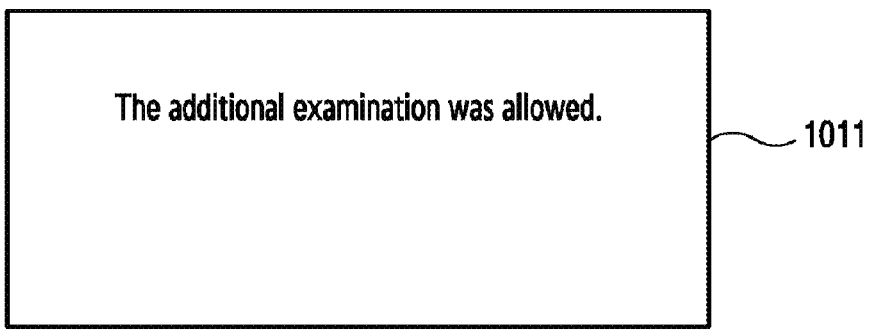
FIG. 10E is a view illustrating an example of a response message displayed on a display of an ultrasound imaging apparatus according to an embodiment of the disclosure.

FIG. 10E is a view illustrating an example of a response message displayed on a display of an ultrasound imaging apparatus according to an embodiment of the disclosure.

Referring to FIG. 10E, when receiving a response signal for allowing an additional examination, the ultrasound imaging apparatus may notify the operator thereof that that the additional examination has been allowed. For example, as illustrated in FIG. 10E, the ultrasound imaging apparatus may display a pop-up message 1011 on the display. In contrast, when receiving a response signal for not allowing the additional examination, the ultrasound imaging apparatus may display, on the display, a pop-up message (not illustrated) notifying the operator thereof that the additional examination has not been allowed.

According to some embodiments of the disclosure, when an additional examination includes multiple additional examination items and an in-charge doctor approves only some additional examination items among the multiple additional examination items, the ultrasound imaging apparatus may display, on the display, only the allowed additional examination items. An operator of the ultrasound imaging apparatus may check the allowed additional examination items, and may perform an allowed additional examination.

Figure 10F:
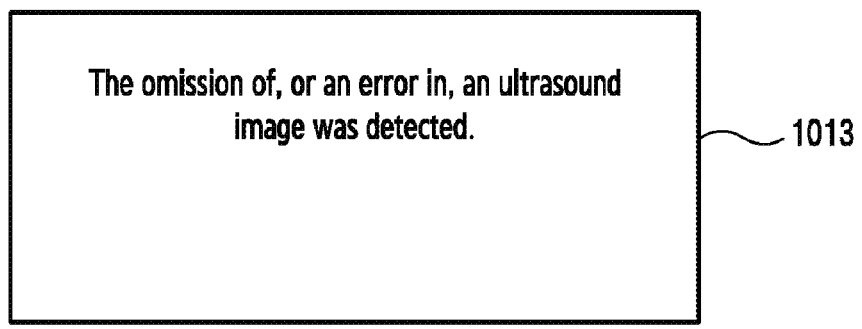
FIGS. 10F and 10G are views each illustrating an example of error information displayed on a display of an ultrasound imaging apparatus according to an embodiment of the disclosure.
Figure 10G:
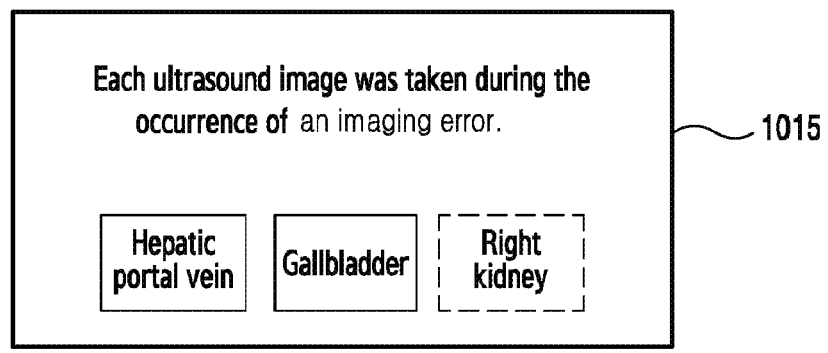

FIGS. 10F and 10G are views each illustrating an example of error information displayed on a display of an ultrasound imaging apparatus according to an embodiment of the disclosure.

Referring to FIGS. 10F and 10G, the ultrasound imaging apparatus (e.g., the ultrasound imaging apparatus 1000) may display error information on the display 1001 (e.g., the display 1400 or 801) on the basis of a result of the analysis of an ultrasound image through a learning network model. For example, when, as the result of the analysis, an inappropriate image or an omitted image exists among the ultrasound images, as illustrated in FIG. 10F, the ultrasound imaging apparatus may display, on the display, a pop-up message 1013 notifying a user of an error.

According to some embodiments of the disclosure, the ultrasound imaging apparatus may provide information on an ultrasound image, which has been taken during the occurrence of an imaging error, among the multiple ultrasound images. For example, as illustrated in FIG. 10G, the ultrasound imaging apparatus may display information on multiple ultrasound images, each of which has been taken during the occurrence of an imaging error, at a lower end part of a pop-up message 1015.

Meanwhile, the ultrasound imaging apparatus may display an inappropriate ultrasound image and an omitted ultrasound image in such a manner as to have a visual difference (such as character color, line type, line thickness, background color, transparency, etc.) therebetween. For example, referring to the pop-up message 1015 of FIG. 10G, ultrasound images obtained by imaging the hepatic portal vein and the gallbladder respectively, each of which is represented using a solid-line box, may signify inappropriate ultrasound images, and an ultrasound image, which is obtained by imaging the right kidney and represented using a dotted-line box, may signify an omitted ultrasound image. This configuration is only an example, and thus, embodiments of the disclosure are not limited thereto. That is, other methods could be used to indicate inappropriate or omitted images, such as text display or various types of icons.

When one ultrasound image is selected from among the ultrasound images taken during the occurrence of an imaging error, the ultrasound imaging apparatus may provide detailed information about the selected ultrasound image. An operator of the ultrasound imaging apparatus may check the detailed information, and may perform re-imaging. According to some embodiments of the disclosure, the operator of the ultrasound imaging apparatus may transmit an ultrasound image, which has been determined as an inappropriate image by an external server or the ultrasound imaging apparatus, to an in-charge doctor, and may inquire of the in-charge doctor about whether re-imaging is to be performed.

In accordance with another aspect of the disclosure, an ultrasound imaging apparatus for imaging a subject comprises: a display configured to display information; and communication unit; a processor configured to: receive ultrasound images from an ultrasound probe; transmit, via the communication unit, the received ultrasound images to an external server, receive, via the communication unit, an analysis of the ultrasound images from the external server, wherein the analysis indicates that at least one additional ultrasound image is required, control the display to display an operating mode for operating the ultrasound imaging apparatus or the ultrasound probe, receive a user input selecting the operating mode, and control the ultrasound imaging apparatus to obtain the at least one additional ultrasound image while the ultrasound imaging apparatus or the ultrasound probe is operating in the selected operating mode.

According to the disclosure, the operating mode is one of: an Amplitude (A) mode, a Brightness (B) mode, a Motion (M) mode, a shearwave mode, or a Doppler mode.

According to the disclosure, the operating mode is a protocol for imaging a specific portion of the subject.

According to the disclosure, the analysis indicates that at least one ultrasound image among the transmitted ultrasound images contains an error, and the processor is further configured to control the display to indicate that the at least one ultrasound image among the transmitted ultrasound images contains an error.

According to the disclosure, the analysis indicates that the transmitted ultrasound images are incomplete with respect to a predetermined protocol, and the processor is further configured to control the display to indicate that the transmitted ultrasound images are incomplete with respect to the predetermined protocol.

In accordance with another aspect of the disclosure, an ultrasound imaging apparatus for imaging a subject comprises: a display configured to display information; and a memory storing a learning network model; a processor configured to: receive ultrasound images from an ultrasound probe, analyze the received ultrasound images with the learning network model and determine that at least one additional ultrasound image is required, control the display to display an operating mode for operating the ultrasound imaging apparatus or the ultrasound probe, receive a user input selecting the operating mode, and control the ultrasound imaging apparatus to obtain the at least one additional ultrasound image while the ultrasound imaging apparatus or the ultrasound probe is operating in the selected operating mode.

The above-described ultrasound imaging apparatus according to various embodiments of the disclosure may obtain an ultrasound image of a subject, and before being transmitted to a doctor, may determine whether the obtained ultrasound image is appropriate, by analyzing the obtained ultrasound image through an external server (e.g., a cloud server) or a hardware or software module (e.g., AI) installed within the ultrasound imaging apparatus. When the ultrasound image is determined to be inappropriate, the ultrasound imaging apparatus may request an operator (e.g., a sonographer) of the ultrasound imaging apparatus to perform re-imaging or additional imaging. At this time, the ultrasound imaging apparatus may provide the operator with information (e.g., an area to be additionally imaged, an imaging direction, imaging conditions, an operating mode, etc.) on ultrasound imaging which is required for the re-imaging or additional imaging. For example, the ultrasound imaging apparatus may display, on the display, a UI that enables a user to select an operating mode for a reexamination or an additional examination. Various embodiments of the disclosure can prevent or minimize re-imaging and/or the occurrence of a misdiagnosis caused by an imaging error (e.g., an imaging omission).

Also, according to various embodiments of the disclosure, when additional imaging is required, an in-charge doctor can be notified of a need for additional imaging, and the additional imaging (or additional examination) can be performed according to the in-charge doctor's determination, so as to prevent unnecessary additional imaging.

Embodiments of the disclosure may be implemented in the form of recording media having recorded thereon computer-executable instructions such as program modules executed by a computer. Computer-readable recording media may be any available media accessible by a computer, and include both volatile and non-volatile media and both detachable and non-detachable media. Also, the computer-readable media may include computer storage media and communication media. The computer storage media include both volatile and non-volatile and both detachable and non-detachable media implemented by any method or technique for storing information such as computer-readable instructions, data structures, program modules, or other data. The communication media typically include computer-readable instructions, data structures, program modules, other data of a modulated data signal, or other transmission mechanisms, and include any information transmission media.

The foregoing description of the embodiments of the disclosure has been presented for illustrative purposes only, and it will be understood by those having ordinary knowledge in the technical field to which the disclosure pertains that various changes in form and details may be made therein without departing from the technical idea or essential features of the disclosure. Therefore, it should be understood that the above-described embodiments of the disclosure have been described for illustrative purposes in all aspects and do not limit the disclosure. For example, elements described in singular form may be implemented in a distributed fashion, and similarly, elements described as being distributed may be implemented in a combined form.

Therefore, the scope of the disclosure is defined by the appended claims rather than the detailed description, and should be construed to include all modifications and variations derived from the meaning and scope of the claims and concept equivalent thereto.

The disclosed embodiments may be implemented by software programs including instructions stored in computer-readable storage media.

A computer is an apparatus capable of fetching a stored instruction from a storage medium and performing an operation according to an embodiment of the disclosure according to the fetched instruction, and may include the ultrasound imaging apparatus according to an embodiment of the disclosure or an external server connected to the ultrasound imaging apparatus through a communication channel.

A computer-readable storage medium may be provided in the form of a non-transitory storage medium. Here, the term "non-transitory" merely implies that a storage medium does not include a signal and is tangible, and does not distinguish between semi-permanent storage of data in the storage medium and temporary storage of data therein.

Also, the methods according to embodiments of the disclosure may be provided as computer program products.

A computer program product may include a software program, a computer-readable storage medium having a software program stored therein, or a product traded from a seller to a purchaser.

For example, a computer program product may include a product (e.g., a downloadable application) which has the form of a software program and is electronically distributed by a manufacturer of an ultrasonic apparatus or through an electronic market (e.g., Google's play store or another app store). For electronic distribution, at least part of a software program may be stored in a storage medium, or may be temporarily generated. In this case, the storage medium may be a storage medium of a server of the manufacturer or electronic market, or a storage medium of a relay server.

What is claimed is:

1. A control method of an ultrasound imaging apparatus, the control method comprising:
    obtaining a first ultrasound image of a subject;
    obtaining a result of an analysis of the first ultrasound image;
    displaying a user interface, which allows selection of an operating mode of the ultrasound imaging apparatus, on a display, based on the result of the analysis;
    receiving a user input for selecting the operating mode of the ultrasound imaging apparatus via the user interface;
    operating the ultrasound imaging apparatus in the operating mode based on the user input;
    obtaining a second ultrasound image while the ultrasound imaging apparatus is operating in selected operating mode;
    transmitting information related to the result of the analysis of the first ultrasound image to at least one external electronic apparatus;
    receiving a response message indicating that an additional ultrasound examination is either permitted or not permitted, from the external electronic apparatus;
    displaying, on the display, the received response message, and
    displaying a user interface on the display which notifies a user that a size measurement of a particular shape included in the first ultrasound image is required, based on the result of the analysis of the first ultrasound image and operating the ultrasound imaging apparatus in a size measurement mode,
    wherein the result of the analysis of the first ultrasound image comprises at least one of whether protocol has been followed, whether the ultrasound image is appropriate for reading, whether the ultrasound image has an appropriate resolution, whether an additional ultrasound image should be taken, or whether to have an additional examination.

2. The control method as claimed in claim 1, wherein obtaining the result of the analysis of the first ultrasound image comprises:
    transmitting the first ultrasound image to an external server through a communication unit; and
    receiving, from the external server, the result of the analysis of the first ultrasound image.

3. The control method as claimed in claim 1, wherein the operating mode corresponds to one of a shear wave mode and a Doppler mode.

4. The control method as claimed in claim 1, further comprising:
    displaying, on the display, a notification that the information related to the result of the analysis of the first ultrasound image has been transmitted.

5. The control method as claimed in claim 4, further comprising displaying, on the display, an interface that permits a user to select whether the information related to the result of the analysis of the first ultrasound image will be transmitted to the at least one external electronic apparatus.

6. The control method as claimed in claim 1, wherein the result of the analysis of the first ultrasound image is generated by a learning network model performing the analysis.

7. An ultrasound imaging apparatus comprising:
    a display;
    a communication unit; and
    a processor configured to:
        be operatively connected to the display and the communication unit,
        obtain a first ultrasound image of a subject,
        obtain a result of an analysis of the first ultrasound image,
        control the display to display a user interface, which allows selection of an operating mode of the ultrasound imaging apparatus, based on the result of the analysis,
        receive a user input for selecting the operating mode of the ultrasound imaging apparatus via the user interface,
        operate the ultrasound imaging apparatus in the operating mode based on the user input,
        obtain a second ultrasound image while the ultrasound imaging apparatus is operating in selected operating mode
        transmit information related to the result of the analysis of the first ultrasound image to at least one external electronic apparatus through the communication unit,
        receive, from the at least one external electronic apparatus, a response message indicating that an additional examination is either permitted or not permitted,
        control the display to display the received response message, and
        control the display to display a user interface for that notifies a user that a measurement of a size of a particular shape included in the first ultrasound image is required, based on the result of the analysis of the first ultrasound image and operating the ultrasound imaging apparatus in a size measurement mode,
    wherein the result of the analysis of the first ultrasound image comprises at least one of whether protocol has been followed, whether the ultrasound image is appropriate for reading, whether the ultrasound image has an appropriate resolution, whether an additional ultrasound image should be taken, or whether to have an additional examination.

8. The ultrasound imaging apparatus as claimed in claim 7, wherein the operating mode corresponds to one of a shear wave mode and a Doppler mode.

9. The ultrasound imaging apparatus as claimed in claim 7, wherein the processor is configured to:
    control the display to display a notification that the information related to the result of the analysis of the first ultrasound image has been transmitted.

10. The ultrasound imaging apparatus as claimed in claim 9, wherein the processor is configured to control the display to display an interface that permits a user to select whether the information related to the result of the analysis of the first ultrasound image will be transmitted to the at least one external electronic apparatus.

11. The ultrasound imaging apparatus as claimed in claim 7, further comprising a memory configured to store a learning network model, wherein the processor is configured to obtain the result of the analysis of the first ultrasound image by applying the stored learning network model to the first ultrasound image.

12. The ultrasound imaging apparatus as claimed in claim 7, wherein the processor is configured to:

transmit the first ultrasound image to an external server that stores a learning network model, through the communication unit, and obtain, from the external server, the result of the analysis of the first ultrasound image.

13. A computer program product including a non-transitory computer-readable recording medium storing a program for executing operations comprising:

obtaining a first ultrasound image of a subject;

obtaining a result of an analysis of the first ultrasound image by using a learning network model;

displaying a user interface, which permits selection of an operating mode of an ultrasound imaging apparatus, on a display, based on the result of the analysis;

receiving a user input for selecting the operating mode of the ultrasound imaging apparatus via the user interface;

operating the ultrasound imaging apparatus in the operating mode based on the user input;

obtaining a second ultrasound image while the ultrasound imaging apparatus is operating in selected operating mode;

transmitting information related to the result of the analysis of the first ultrasound image to at least one external electronic apparatus;

receiving a response message indicating that an additional ultrasound examination is either permitted or not permitted, from the external electronic apparatus;

displaying, on the display, the received response message, and displaying a user interface on the display which notifies a user that a size measurement of a particular shape included in the first ultrasound image is required, based on the result of the analysis of the first ultrasound image and operating the ultrasound imaging apparatus in a size measurement mode, wherein the result of the analysis of the first ultrasound image comprises at least one of whether protocol has been followed, whether the ultrasound image is appropriate for reading, whether the ultrasound image has an appropriate resolution, whether an additional ultrasound image should be taken, or whether to have an additional examination.

14. The computer program product as claimed in claim 13, wherein the recording medium further stores a program for executing operations comprising:

displaying, on the display, a notification that the information related to the result of the analysis of the first ultrasound image has been transmitted.

15. The computer program product as claimed in claim 13, wherein the recording medium further stores a program for executing operations comprising:

transmitting the first ultrasound image to an external server that stores the learning network model; and obtaining the result of the analysis of the first ultrasound image from the external server.

* * * * *